(12) United States Patent
Adhvaryu

(10) Patent No.: US 7,592,297 B2
(45) Date of Patent: Sep. 22, 2009

(54) ANTI-FRICTION ANTI-WEAR LUBRICANT ADDITIVE

(75) Inventor: Atanu Adhvaryu, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 149 days.

(21) Appl. No.: 11/589,978

(22) Filed: Oct. 31, 2006

(65) Prior Publication Data

US 2008/0103073 A1    May 1, 2008

(51) Int. Cl.
*C10M 173/00* (2006.01)
*C07C 51/00* (2006.01)

(52) U.S. Cl. ............... 508/431; 508/487; 508/491; 554/124; 554/148; 554/213

(58) Field of Classification Search ........... 508/431, 508/487, 491; 554/124, 213, 148
See application file for complete search history.

(56) References Cited

U.S. PATENT DOCUMENTS

| 5,552,070 | A | 9/1996 | Schafer et al. |
|---|---|---|---|
| 2006/0009365 | A1 | 1/2006 | Ehran et al. |

FOREIGN PATENT DOCUMENTS

| DE | 1 812 849 | 6/1970 |
|---|---|---|
| DE | 32 08 748 | 9/1983 |
| GB | 2 273 503 | 11/1993 |
| WO | WO 98/13442 | 4/1998 |

OTHER PUBLICATIONS

Jie et al.: "1H-Nuclear magnetic resonance spectroscopic studies of saturated, acetylenic and ethylenic triacylgycerols," Chemistry and Physics of Lipids, vol. 77, No. 2, Aug. 25, 1995, pp. 155-171, XP009096511 ISSN: 0009-3084 p. 160; table 1; compound 8.
Database WPI Week 197345, Thomson Scientific, London, GB; AN 1973-68237U, XP 002475935 & SU 371 239 A of Feb. 22, 1974, Biophys Inst Health Min U.
Blackman et al.: "Promotors for the dropwise condensation of steam. Part II. Preparation of compounds containing polyfunctional sulphur groups", Journal of the American Chemical Society, No. 1, 1957, pp. 165-169, XP00233423, ISSN: 0002-7863, p. 168.
Nguyen H-P et al.: "Hydrolyse des sels internes de phosphate d'isothiouronium: preparation des derives monosubstitues de l'acide o-phosphorique," Comptes Rendus Hebdomadaires des Seances de L'Academie des Sciences, Serie C: Sciences Chimiques, vol. 279, Feb. 26, 1973, pp. 799-801, XP009098019.
Mizrakh et al.: "Phosphorus-containing thiouronium derivatives. II. Cleavage of 1,3,2-dioxaphospholane and 1,3,2-dioxaphosphorinane rings by thiourea," Journal of General Chemistry USSR, vol. 42, Aug. 1972, pp. 1690-1694, XP009098020, ISSN: 0022-1279.
Princen L. H., et al., "Development of New Crops for Industrial Raw Materials", JAOCS, vol. 61, No. 2, pp. 281-289, Feb. 1984.
Kammann Jr., Karl P., et al., "Sulfurized Vegetable Oil Products as Lubricant Additives", JAOCS, vol. 62, No. 5, pp. 917-923, May 1985.
Miwa Thomas K., et al., "Sulfurized Jojoba Oil as Extreme-Pressure Lubricant", Proc. Second Int. Conf. On Jojoba and Its Uses, pp. 253-264, Ensenada, Baja California, Norte, Mexico, 1976.
Molenda Jaroslaw, et al., "Unsaturated Oxygen Compounds as Antiwear Additives for Lubricants", Tribologia, pp. 323-331, Mar. 1999.
Qureshi Shahid, et al., "Simultaneous Interpenetrating Networks from Epoxidized Triglyceride", Polymer Science and Technology, vol. 17, pp. 249-271, Plenum Press, 1983.

*Primary Examiner*—Rosalynd Keys
*Assistant Examiner*—Yate' K Cutliff
(74) *Attorney, Agent, or Firm*—Finnegan, Henderson, Farabow, Garrett & Dunner

(57) ABSTRACT

The present disclosure is directed to compounds and methods of making the compounds (3, 5) having the formula:

$$\begin{aligned}
&CH_2-O-\underset{\underset{O}{\|}}{C}-(CH_2)_7-(CH-CH)_n\text{---}CH_3\\
&\phantom{CH_2-O-C-(CH_2)_7-}\phantom{(}\underset{X}{|}\phantom{-}\underset{OH}{|}\\
&CH-O-\underset{\underset{O}{\|}}{C}-(CH_2)_7-(CH-CH)_n\text{---}CH_3\\
&\phantom{CH-O-C-(CH_2)_7-}\phantom{(}\underset{X}{|}\phantom{-}\underset{OH}{|}\\
&CH_2-O-\underset{\underset{O}{\|}}{C}-(CH_2)_7-(CH-CH)_n\text{---}CH_3\\
&\phantom{CH_2-O-C-(CH_2)_7-}\phantom{(}\underset{OH}{|}\phantom{-}\underset{X}{|}
\end{aligned}$$

where X is a functional group chosen from:

$$\underset{RO}{\overset{RO}{\diagdown}}\underset{\|}{\overset{P}{\diagup}}\overset{O}{\underset{O}{\diagdown}}\quad\text{and}\quad NH\underset{NH_2}{\overset{\|}{\diagdown}}S\diagdown\diagup O\underset{\|}{\overset{P}{\diagdown}}\overset{O}{\underset{OR}{\diagup}}$$

and wherein R is chosen from hydrogen, n-alkyl, iso-alkyl, aryl, heterocyclic ring, and nitrogen or a sulfur containing group, and n ranges from 0 to 4.

20 Claims, No Drawings

ANTI-FRICTION ANTI-WEAR LUBRICANT ADDITIVE

TECHNICAL FIELD

The present disclosure relates generally to a lubricant additive, and more particularly, to a lubricant additive to improve the anti-friction and anti-wear properties of a lubricant.

BACKGROUND

A lubricant is a substance introduced between two moving surfaces to reduce the friction and wear between them. Lubrication occurs when the opposing surfaces are separated by the lubricant (typically a fluid). In general, four regimes of lubrication are broadly defined based upon the mechanism by which the lubricant operates to reduce friction and wear between the moving parts. They are hydrodynamic regime (where a thick film of fluid separates the moving surfaces), mixed regime (where a thin film separates the moving surfaces), boundary regime (where most of the lubricant is squeezed out from between the moving parts), and enhanced pressure regime (where substantially all the liquid is squeezed out from between the moving parts and a thin solid film is formed on the surface of the moving parts). Lubricants are typically made by blending a base oil (most often petroleum fractions) with any number of additives. The additives impart special properties, such as reduced friction, reduced wear, increased viscosity, improved viscosity index, resistance to corrosion, oxidation, aging, and/or contamination, etc. to the lubricant. The functional group contained in the most commonly used anti-wear and anti-friction additives are boron (B), copper (Cu), phosphorous (P), sulfur (S), nitrogen (N), lead (Pb), and/or zinc (Zn).

Many of the lubricants and some additives currently being used are made of petroleum products that are toxic, making it increasingly difficult for safe and easy disposal. There has been an increasing demand for environmentally safe lubricants in recent years due to concerns regarding accidental spillage or leakage of the lubricants and increasingly strict government regulations restricting their use.

U.S. Patent Publication 2006/0009365 A1 issued to Erhan et al. (hereinafter the '365 publication) describes a sulfur modified vegetable oil that can be used as an additive for a lubricant. In the '365 publication, the lubricant additives are created by reacting epoxidized triglyceride oils (vegetable oil) with thiols (having the general formula HS—R'''). The resulting sulfur containing poly (hydroxy thioether) derivatives are environmentally safe because they are formed by modifying a vegetable oil.

Although the lubricant additive of the '365 publication may be environmentally safe, it may have some performance limitations. The sulfur containing additives of the '365 publication have the structural formula:

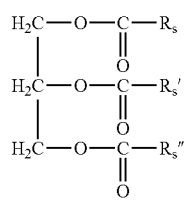

Formula 1 where $R_s$, $R_s'$, $R_s''$ are characterized by the formula:

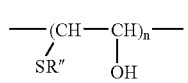

Formula 2 where R''' is hydrogen, a C1 to C22 hydrocarbon, 4-6 member heterocyclic ring, or a mixture thereof.

The additive of the '365 publication is restricted to sulfur as the functional group. Therefore, the additive does not offer flexibility in designing an additive with a different functional group which may be more suited to an application. For instance, the additive cannot be designed with phosphorous or an amine as the functional group to suit a particular application. In addition, the presence of the thio-ether group (C—SR''') and the hydroxyl group (C—OH) in the additive of the '365 publication (see Formula 2) leads to a higher viscosity because of the inter and intra molecular hydrogen bonding within the thio-ether molecules.

The present disclosure is directed at overcoming one or more of the shortcomings of the prior art anti-friction and anti-wear lubricant additives.

SUMMARY OF THE INVENTION

In one aspect, the present disclosure is directed to a compound having the formula:

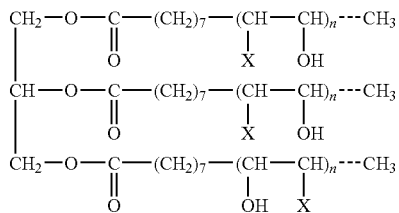

where X is a functional group chosen from:

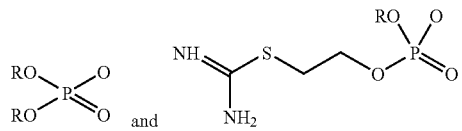

and R is chosen from hydrogen, n-alkyl, iso-alkyl, aryl, heterocyclic ring, and nitrogen or sulfur containing group. The value of n in the compound ranges from 0 to 4.

In another aspect, the present disclosure is directed to a method of making a compound having the formula:

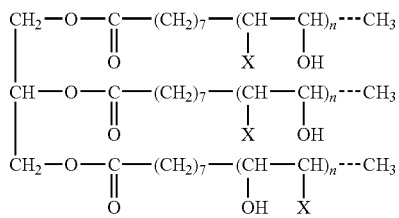

where X is a functional group chosen from:

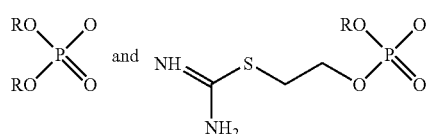

and R is chosen from hydrogen, n-alkyl, iso-alkyl, aryl, heterocyclic ring, and nitrogen or sulfur containing group. The value of n in the compound ranges from 0 to 4. The method includes at least the step of changing an epoxidized seed oil to the compound.

DETAILED DESCRIPTION

The anti-friction and anti-wear additives of the current disclosure may be sulfur (S), phosphorous (P) and/or an amine ($NH_2$) group bearing structures. They are formed by reacting a commercially available epoxy seed oil starting material with a reagent containing sulfur (S), phosphorous (P) and/or an amine ($NH_2$) group molecules, under selected conditions. The resulting additive compound (the final product of the reaction) retains the natural functional properties, such as high flash point, amphiphilic character, surface active sites, high molecular weight, etc., of the vegetable oil. In addition, the additive compound may also contain S, P and/or $NH_2$ molecules to produce functional groups that generate a stable chemical boundary film to reduce friction and wear during metal-metal contact.

The starting material may be derived by epoxidizing commonly available seed oils having a triglyceride structure with at least one site of unsaturation. The seed oil may include, but not limited to, vegetable oils, plant oils and plant-like synthetic and semi-synthetic triglycerides. For example, the epoxy seed oil starting material may be derived by epoxidizing cotton seed oil, soybean oil, castor oil, canola oil, sunflower oil, corn oil, tung oil, palm oil peanut oil, grape oil, or other common seed oils. A generic C18 seed oil structure and an epoxy seed oil structure are represented by the following formula:

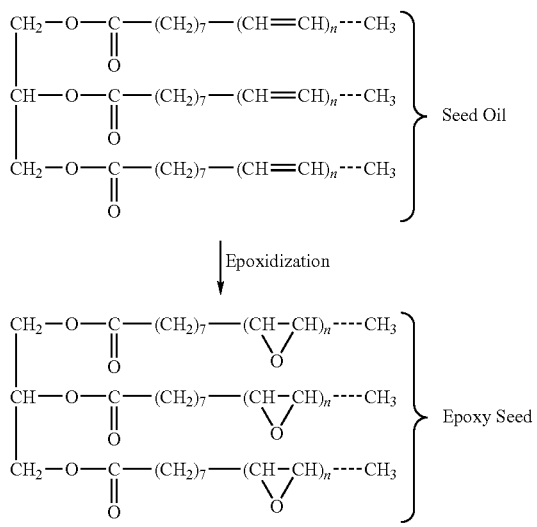

Formula 3 wherein n represents the number of unsaturated sites. The number of these unsaturated sites can range from 0 to 4. The epoxy seed oil may retain the basic molecular structure of seed oil but may have its unsaturated sites (carbon double bonds C=C) replaced with epoxy rings (oxirane ring —C—O—C—), that is, epoxidized. In some applications more than 90% of the unsaturated sites may be epoxidized. The degree of epoxidization may be such that there can be at least 2 (such as at least 3) oxirane rings per molecule of the seed oil. For example, epoxidized soybean oil having 3-7 oxirane rings per molecule may be used as the starter material. It is contemplated that in some applications, a seed oil may be epoxidized to be used as the starting material, while in other applications a commercially available epoxy seed oil may be used as the starting material. Any known process, such as that described by Qureshi et al. (Polymer Science and Technology, Vol. 17, Plenum Press, p. 250), which is incorporated by reference herein, may be used for epoxidizing the seed oil.

From the epoxidized seed oil, the compound can be formed. In at least one embodiment, the epoxidized seed oil may be reacted with an organophosphorous acid derivative. Organophosphorous acid derivatives include, but are not limited to, phosphorous, thiophosphorous, or aminothiophosphorous containing acid or their derivatives. For example, 2-carbamimidoylsulfanylethoxy-ethoxy-phosphinic acid anhydride ($C_5H_{12}N_2O_7P_2S$), which is an organophosphorous acid anhydride, may serve as the reagent. These reagents may be represented by the structural formulas:

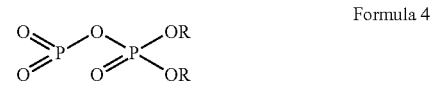

Formula 4

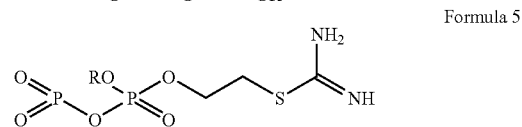

Formula 5 wherein R is chosen from a hydrogen (H), n-alkyl, iso-alkyl, aryl, heterocyclic ring, and N or S containing group.

The reaction of the epoxy seed oil starting material with the reagent may be a one-step or a two-step process. For both the one-step and the two-step processes, the ratio of the starting material to the reagent may be between approximately 1:3 and 1:8. In some applications, the ratio of the starting material to the reagent may be around 1:5.

In the one step process, the epoxy seed oil may be reacted with the reagent under controlled conditions at room or slightly elevated temperature. The reaction temperature may depend upon the reagent, and in some cases may be (or slightly exceed) the refluxing temperature of the reagent. This reaction temperature may range, for example, from about 50° C. to about 200° C., and may take place in an inert atmosphere in an organic solvent media, such as methylene chloride. In some cases, $N_2$ gas may be bubbled through the reaction mixture to create an inert atmosphere. The one-step reaction of the starting material with the reagent represented by Formula 4 is exemplified by the formula:

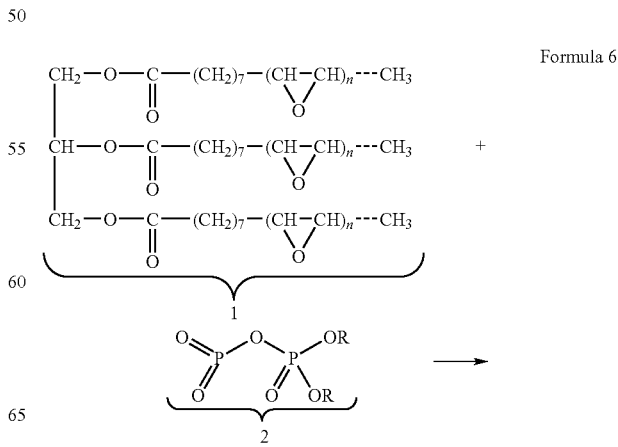

Formula 6

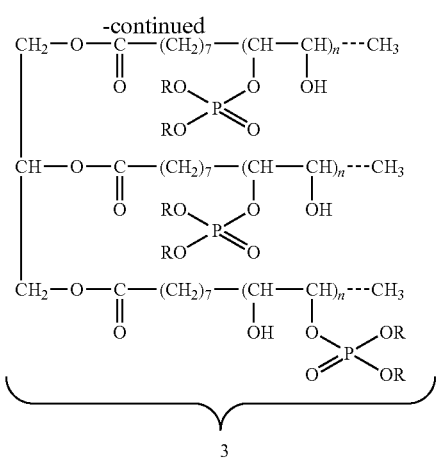

wherein 1 represents the epoxy seed oil, 2 represents the reagent, and 3 represents an embodiment of the resulting lubricant additive. The one-step reaction of the starting material with the reagent represented by Formula 5 is exemplified by the formula:

Formula 7

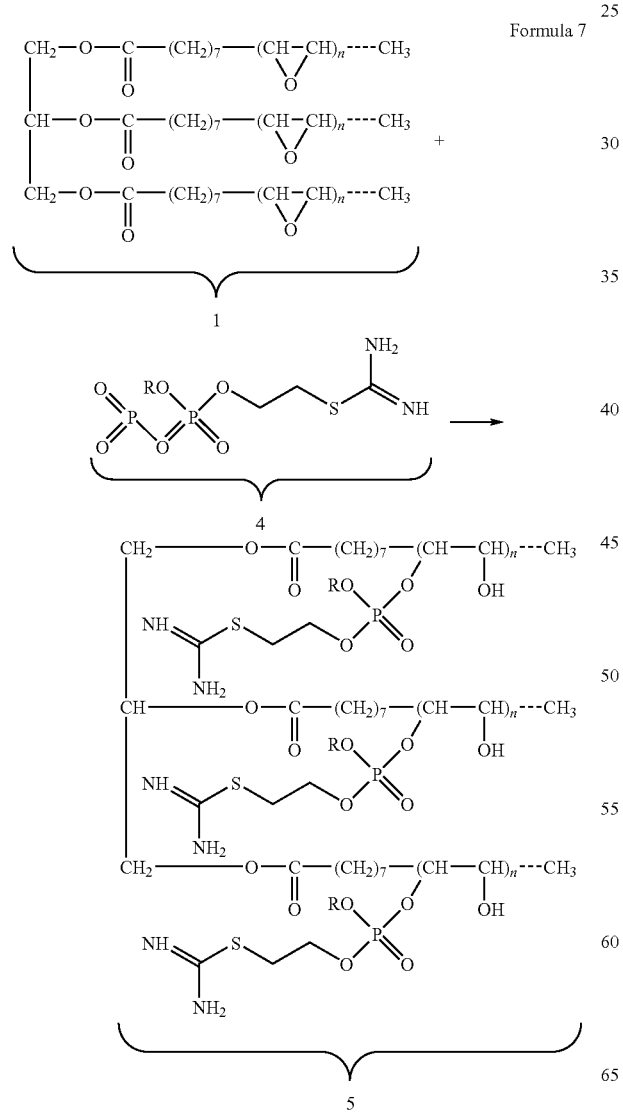

wherein 1 represents the epoxy seed oil, 4 represents the reagent, and 5 represents another embodiment of the resulting lubricant additive.

As represented in Formulas 6 and 7, each fatty acid chain of the lubricant additive 3 or 5 has an adjacent hydroxyl group and a phophate-ester (or thioaminophosphorous) group (the functional groups) attached to a carbon of the opened epoxy ring (CH—CH) structure. Those functional groups may be attached to either of the carbon atoms in the opened epoxy ring structure. In some cases, the functional groups may be attached on all the opened epoxy ring structures in the epoxy seed oil molecule, while in other cases, the functional groups may be attached to only some of the epoxy rings in the epoxy seed oil molecule. In other words, the epoxy seed oil may have one or more of its unsaturated sites replaced by the functional groups. In some applications, more than 90% of the unsaturated sites may be replaced by the functional groups.

The two-step process may include two distinct steps to create the final lubricant additive. In the first step, a di-hydroxylated (di-OH) product of the epoxy seed oil may be formed by reacting the epoxy seed oil under controlled conditions with water ($H_2O$) in the presence of a mild acid catalyst ($H^+$), such as perchloric acid ($HClO_4$), at around 100° C. The chemical reaction of the first step in the two-step process may be exemplified by the following reaction:

Formula 8

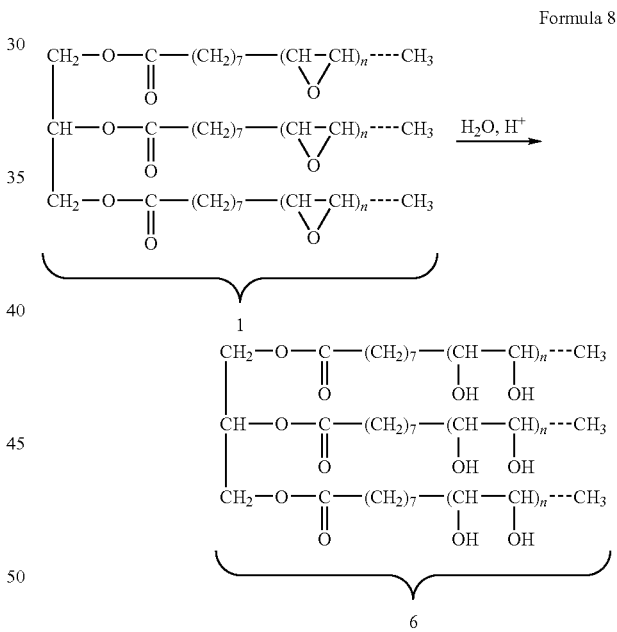

wherein 1 represents the epoxy seed oil and 6 represents the di-hydroxylated product. That di-hydroxylated product may be separated and may serve as the starter material in the second step of the two-step process.

In the second step of the two-step process, the di-hydroxylated product, obtained from the reaction in the first step (Formula 8), may be reacted with an organophosphorous acid derivative (for instance, an organophosphorous acid anhydride), such as one of the reagents described by Formula 4 and Formula 5, to produce the lubricant additive. The reaction temperature may depend upon the selection of the reagent and in some cases may range from about 50° C. to about 200° C., and take place in an inert atmosphere in an organic solvent media. In some cases, N$_2$ gas may be bubbled through the reaction mixture to create an inert atmosphere.

Depending upon the reagent used (that represented by Formula 4 or Formula 5), the chemical reaction of the second step in the two-step process may be exemplified by the following reactions:

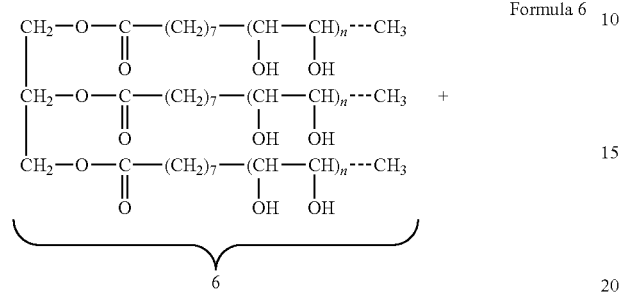

wherein 6 represents the di-hydroxylated product of the epoxy seed oil, 2 and 4 represents the reagents used, and 3 and 5 represent embodiments of the resulting lubricant additive. As in the reactions exemplified by Formulas 6 and 7, the reagent addition may take place on either carbon atom of the opened epoxy chain. Also, in some cases reagent additions may take place in substantially all the epoxy chains while in other cases, reagent addition may take place only at a few sites.

The final lubricant additive (3 and 5) obtained in each case (Formula's 6, and 7) may be dictated by the reagent used, and may consist of a mixture of the epoxy seed oil and the lubricant additive. The conversion efficiency of the epoxy seed oil to the lubricant additive may range from about 50% to about 90% depending upon the reagent and the process used (one-step or two-step) for the conversion. The final lubricant may have the functional group (derived from the reagent used) attached to the primary oil molecular structure. The final lubricant obtained following the one-step or the two-step process may be further purified, for example, using solvent washing.

INDUSTRIAL APPLICABILITY

The disclosed lubricant additive may be used with any lubricant used to reduce friction and wear between parts. For example, the additives of the current disclosure may be used with lubricant oils used in internal combustion engine or any other machine applications. The disclosed lubricant additives are made from seed oils that are environmentally safe and provide excellent hydrodynamic lubricity. The epoxy seed oils are chemically modified to attach selected functional groups in the epoxy seed oil molecule to improve the lubrication characteristics of the epoxy seed oil in the extreme pressure regime of lubrication. The chemical modification can preserve the inherent hydrodynamic lubrication characteristics of the epoxy seed oil, while imparting enhanced lubrication characteristics in the enhanced pressure lubrication regime. In order to better illustrate the disclosed lubricant additives, a one-step and a two-step process of making a lubricant additive covered in this disclosure is described.

Following the one-step process, commercially available 98% pure epoxidized soybean oil may be dissolved in an organic solvent methylene chloride and used as the starting material. Perchloric acid may be added drop-wise into the starting material. The organophosphorous acid anhydride reagent, $C_5H_{12}N_2O_7P_2S$, may then be added to the mixture drop-wise to the mixture in the approximate ratio 5:1. The reaction mixture may be stirred continuously for good mixing. Nitrogen gas may be bubbled through the mixture to maintain an inert ambient. The mixture may be heated and maintained at about 60° C. for about 4 hours. After the reaction is complete, the mixture may be cooled to room temperature and the organic phase washed with sodium bicarbonate solution and DI water. The organic phase may then be further dried using anhydrous magnesium sulfate, filtered and solvent removed by distillation to obtain the lubricant additive.

Following the two-step process, commercially available 98% pure epoxidized soybean oil may be mixed with excess water and stirred vigorously. To this mixture, perchloric acid may be added drop-wise and the resulting mixture heated and maintained at about 100° C. for about 4 hours. The reaction mixture may be cooled and the organic phase extracted with the organic solvent methylene chloride. The dihydroxylated oil may then be recovered by removing the solvent by vacuum distillation. The recovered dihydroxylated oil may then be reacted with the organophosphorous acid anhydride reagent, $C_5H_{12}N_2O_7P_2S$. The reaction may be maintained in an inert atmosphere using nitrogen gas. The reaction mixture may be heated to about 60° C. and maintained at this temperature for about 4 hours. The reaction mixture may be stirred while being maintained at the 60° C. temperature. After the reaction is complete, the mixture may be cooled to room temperature and the organic phase washed with sodium bicarbonate solution and DI water. The organic phase may be further dried using anhydrous magnesium sulfate, filtered, and solvent removed by distillation to obtain the lubricant additive.

The additives of the current disclosure can be designed with a functional group comprising sulfur, phosphorous and/or amine groups depending upon the reagent used. Therefore, the additives can be tailored to generate selected functional groups suited for a particular application.

The additives of the current disclosure can also have a low viscosity. The bulk of the functional groups attached to the epoxy seed oil molecule can reduce the free hydrogen bonding sites available, thereby leading to a low viscosity.

It will be apparent to those skilled in the art that various modifications and variations can be made to the disclosed lubricant additives and the method of making them. Other embodiments will be apparent to those skilled in the art from consideration of the specification and practice of anti-friction and anti-wear additives for lubricants. It is intended that the specification and examples be considered as exemplary only, with a true scope being indicated by the following claims and their equivalents.

What is claimed is:

1. A compound having the formula:

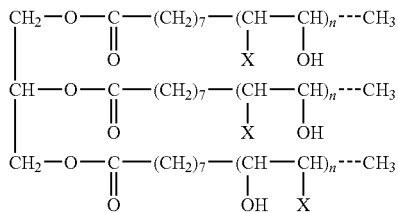

wherein X is a functional group chosen from:

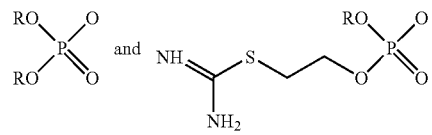

wherein R is chosen from hydrogen, n-alkyl, iso-alkyl, aryl, heterocyclic ring, and nitrogen or sulfur containing group; and n ranges from 1 to 4.

2. The compound of claim 1, wherein n is greater than or equal to 3.

3. A method of making a compound having the formula:

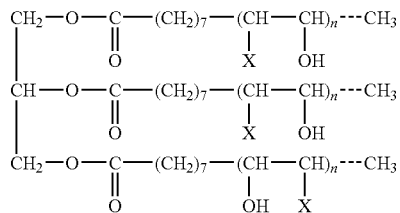

wherein, X is a functional group chosen from:

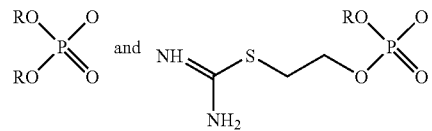

wherein, R is chosen from hydrogen, n-alkyl, iso-alkyl, aryl, heterocyclic ring, and nitrogen or sulfur containing group; n ranges from 1 to 4; and comprising at least the step of:

changing an epoxidized seed oil to the compound.

4. The method of claim 3, further comprising producing the epoxidized seed oil from a seed oil by converting an unsaturated carbon-carbon double bond to an epoxy ring.

5. The method of claim 4, wherein converting an unsaturated carbon-carbon double bond to an epoxy ring comprises converting at least 90% of the unsaturated carbon-carbon double bonds to epoxy rings.

6. The method of claim 3, wherein changing an epoxidized seed oil to the compound comprises reacting the epoxidized seed oil with an organophosphorous acid derivative.

7. The method of claim 6, wherein reacting the epoxidized seed oil comprises mixing the epoxidized seed oil with the organophosphorous acid derivative in the approximate ratio 1:5.

8. The method of claim 6, wherein reacting the epoxidized seed oil further comprises heating the epoxidized seed oil and the organophosphorous acid derivative to a temperature ranging from about 50° C. to about 200° C.

9. The method of claim 6, wherein reacting the epoxidized seed oil further comprises performing the reaction in an inert atmosphere.

10. The method of claim 3, wherein changing an epoxidized seed oil to the compound comprises:
   converting the epoxidized seed oil to a dihydroxylated oil, and
   chemically changing the dihydroxylated oil to the compound.

11. The method of claim 10, wherein converting the epoxidized seed oil to a dihydroxylated oil comprises treating the epoxidized seed oil with water and a mild acid.

12. The method of claim 11, wherein the mild acid is perchloric acid ($HClO_4$)

13. The method of claim 11, wherein changing the epoxidized seed oil to a dihydroxylated oil further comprises heating the epoxidized seed oil.

14. The method of claim 10, wherein chemically changing the dihydroxylated oil to the compound comprises reacting the dihydroxylated oil with an organophosphorous acid derivative.

15. The method of claim 14, wherein reacting the dihydroxylated oil comprises mixing the dihydroxylated oil with the organophosphorous acid derivative in an approximate ratio of 1:5.

16. The method of claim 14, wherein the organophosphorous acid derivative is 2-carbamimidoylsulfanylethoxy-ethoxy-phosphinic acid anhydride.

17. The method of claim 3, whereinchanging an epoxidized seed oil to the compound comprises purifying the compound by solvent washing.

18. A lubricant containing a compound having the formula:

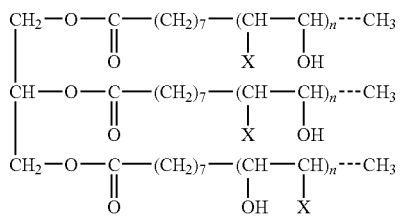

wherein X is a functional group chosen from:

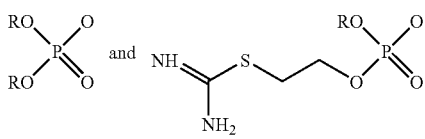

wherein R is chosen from hydrogen, n-alkyl, iso-alkyl, aryl, heterocyclic ring, and nitrogen or sulfur containing group; and n ranges from 1 to 4.

19. The lubricant of claim 18, wherein n is greater than or equal to 3.

20. The method of claim 14, wherein the epoxidized seed oil is heated to a temperature of about 100° C.

* * * * *